United States Patent [19]

Möller et al.

[11] 3,992,404
[45] Nov. 16, 1976

[54] PYRAZOL-5-ONES

[75] Inventors: Eike Möller; Karl Meng, both of Wuppertal; Egbert Wehinger, Neviges; Harald Horstmann, Wuppertal, all of Germany

[73] Assignee: Bayer Aktiengesellschaft, Germany

[22] Filed: May 19, 1975

[21] Appl. No.: 578,516

Related U.S. Application Data

[62] Division of Ser. No. 461,285, April 15, 1975, Pat. No. 3,952,008.

[30] Foreign Application Priority Data

Apr. 17, 1973 Germany............................ 2319279
Dec. 19, 1973 Germany............................ 2363138

[52] U.S. Cl............................ 260/310 A; 424/273
[51] Int. Cl.$^2$.............. C07D 231/20; C07D 231/38; C07D 231/52
[58] Field of Search................................ 260/310 A

[56] References Cited
UNITED STATES PATENTS

| | | | |
|---|---|---|---|
| 2,376,380 | 5/1945 | Porter et al. | 260/305 |
| 2,476,986 | 7/1949 | Martin | 260/310 |
| 2,476,987 | 7/1949 | Martin | 260/310 |
| 2,600,788 | 6/1952 | Lorin et al. | 95/6 |
| 2,619,419 | 11/1952 | Jennen | 95/6 |
| 2,672,417 | 3/1954 | Jennen | 95/6 |
| 2,681,915 | 6/1954 | Gysin et al. | 260/310 |
| 3,113,949 | 12/1963 | Bicking | 260/310 |
| 3,153,654 | 10/1964 | Ficken | 260/310 |
| 3,558,319 | 1/1971 | Hamaoka et al. | 96/100 |
| 3,615,502 | 10/1971 | Yoshida | 96/56.5 |
| 3,632,818 | 1/1972 | Allais et al. | 260/310 A |
| 3,694,456 | 9/1972 | Noguchi et al. | 260/310 R |
| 3,719,764 | 3/1973 | Girault et al. | 424/273 |
| 3,812,145 | 5/1974 | Sato et al. | 260/310 A |
| 3,823,156 | 7/1974 | Oka et al. | 260/310 A |

FOREIGN PATENTS OR APPLICATIONS

| | | |
|---|---|---|
| 2,068,413 | 8/1971 | France |
| 2,230,792 | 1/1974 | Germany |
| 2,230,675 | 1/1974 | Germany |
| 1,190,914 | 5/1970 | United Kingdom |

*Primary Examiner*—Donald B. Moyer

[57] ABSTRACT

1-Substituted pyrazole-5-ones of the formula

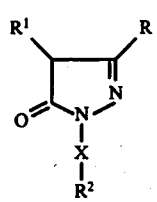

and pharmaceutically acceptable, nontoxic salts thereof, wherein
R is hydrogen or amino;
R$^1$ is hydrogen, alkyl, alkenyl, unsubstituted or substituted aryl or unsubstituted or substituted aralky;
X is
a. ethylene, ethylene wherein 1 hydrogen atom on one of the carbon atoms is substituted by alkyl of 1 to 4 carbon atoms, ethylene wherein 1 hydrogen atom on each of the two carbon atoms is substituted by alkyl of 1 to 4 carbon atoms or said ethylene which is linked to R$^2$ via an oxygen or sulphur atom;
b. propenyl, propenyl wherein 1 hydrogen atom on one, two or three of the carbon atoms is substituted by alkyl of 1 to 4 carbon atoms, said propenyl being linked to the N$^1$ atom of the pyrazol ring via its methylene moiety; or
c. methylene;
provided that when X is methylene, R$^1$ is not hydrogen if R is amino;
R$^2$ is aryl unsubstituted or substituted by:
a. 1 or 2 of the same or different substituents selected from the group consisting of halogen, trifluoromethyl, alkyl of 1 to 8 carbon atoms, alkenyl of 2 to 8 carbon atoms and lower alkoxy;
b. cycloalkyl of 5, 6 or 7 carbon atoms of cycloalkenyl of 5, 6 or 7 carbon atoms,
c. alkylamino, dialkylamino, cyano, trifluoromethoxy, nitro, carbamoyl, alkylcarbamoyl, dialkylcarbamoyl, or said carbamoyl wherein the nitrogen atom is a member of a heterocyclic ring, sulphamyl, alkylsulphamyl, dialkylsulphamyl, or said sulphamyl wherein the nitrogen is a member of a heterocyclic ring, or —SO$_n$ alkyl wherein n is 0, 1 or 2;
d. alkylamino, dialkylamino, cyano, trifluoromethoxy, nitro, carbamoyl, alkylcarbamoyl, dialkylcarbamoyl, or said carbamoyl wherein the nitrogen atom is a member of a heterocyclic ring, sulphamyl, alkylsulphamyl, dialkylsulphamyl or said sulphamyl wherein the nitrogen is a member of a heterocyclic ring, or —SO$_n$— alkyl wherein n is 0, 1 or 2, and 1 or 2 of the same or different substituents selected from the group consisting of alkyl, alkenyl, alkoxy, halogen, and trifluoromethyl; or
e. a fused, saturated or unsaturated 5-, 6-, or 7-membered ring or said ring containing 1 or 2 oxygen or sulphur atoms;

are useful for their diuretic, saluretic, antihypertensive and antithrombotic effects.

11 Claims, No Drawings

PYRAZOL-5-ONES

CROSS-REFERENCE

This is a division of Ser. No. 461,285 filed Apr. 15, 1975 now U.S. Pat. No. 3,952,008.

The present invention relates to 1-substituted pyrazol-5-ones, processes for their production, pharmaceutical compositions useful for effecting diuresis, saluresis and for treating hypertension and thromboses in humans and animals wherein said 1-substituted pyrazol-5-ones are the active agent, and to methods of effecting diuresis and saluresis in humans and animals and methods of treating hypertension and thromboses in humans and animals which comprises administering said compounds to such humans or animals.

3-Aminopyrazoles have already been used as color-coupling agents for color photography (A. Weissberger et al., J. Amer. Chem. Soc., 64, 2183 (1942)) and intermediate products for the preparation of color-coupling agents (British Pat. No. 599,919; U.S. Pat. No. 2,367,523; U.S. Pat. No. 2,376,380; U.S. Pat. No. 2,511,231; U.S. Pat. No. 2,600,788; U.S. Pat. No. 2,619,419; U.S. Pat. No. 2,672,417).

Certain pyrazol-5-one derivatives are also used as antipyretics, analgesics and antiphlogistics (compare G. Ehrhart and H Ruschig, Arnzneimittel (Medicines), Volume 1, page 148 (1972)).

We have now discovered a new group of 1-substituted pyrazol-5-ones which have strong diuretic, saluretic, anti-hypertensive and antithrombotic properties.

More particularly, the present invention is concerned with 1-substituted pyrazol-5-ones of the formula

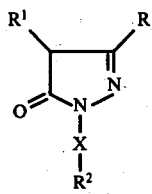

or a pharmaceuticaly acceptable, nontoxic salt thereof wherein

R is hydrogen or amino;

$R^1$ is hydrogen, alkyl, preferably lower alkyl, alkenyl, preferably lower alkenyl, aryl, preferably monoaryl, unsubstituted or substituted by lower alkoxy, or aralkyl, preferably wherein the aryl moiety is a monoaryl moiety and the alkyl moiety is a lower alkyl moiety, said aralkyl being either unsubstituted or substituted by lower alkoxy;

X is
  a. ethylene, ethylene wherein 1 hydrogen atom on one of the carbon atoms is substituted by alkyl of 1 to 4 carbon atoms, ethylene wherein 1 hydrogen atom on each of the two carbon atoms is substituted by alkyl of 1 to 4 carbon atoms or said ethylene which is linked to $R^2$ via an oxygen or sulphur atom;
  b. propenyl, propenyl wherein 1 hydrogen atom on one, two or three of the carbon atoms is substituted by alkyl of 1 to 4 carbon atoms, said propenyl being linked to the $N^1$ atom of the pyrazol ring via its methylene moiety; or
  c. methylene;

provided that when X is methylene, $R^1$ is not hydrogen if R is amino;

$R^2$ is aryl preferably aryl of 6 to 10 carbon atoms, unsubstituted or substituted by
  a. 1 or 2 of the same or different substituents selected from the group consisting of halogen, trifluoromethyl, alkyl of 1 to 8 carbon atoms, alkenyl or 2 to 8 carbon atoms and lower alkoxy;
  b. cycloalkyl of 5, 6 or 7 carbon atoms or cycloalkenyl of 5, 6 or 7 carbon atoms;
  c. alkylamino, preferably lower alkylamino, dialkylamino, preferably di(lower alkyl)amino, cyano, trifluoromethoxy, nitro, carbamoyl, alkylcarbamoyl, preferably lower alkylcarbamoyl, dialkylcarbamoyl, or said carbamoyl wherein the nitrogen atom is a member of a heterocyclic ring, sulphamyl, alkylsulphamyl, preferably lower alkylsulphamyl, dialkylsulphamyl, preferably di(lower alkyl) sulphamyl, or said sulphamyl wherein the nitrogen is a member of a heterocyclic ring, or $-SO_n$ alkyl, preferably lower alkyl, wherein $n$ is 0, 1 or 2;
  d. alkylamino, preferably lower alkylamino, dialkylamino, preferably di(lower alkyl) amino, cyano, trifluoromethoxy, nitro, carbamoyl, alkylcarbamoyl, preferably lower alkylcarbamoyl, dialkylcarbamoyl, preferably di(lower alkyl)carbamoyl, or said carbamoyl wherein the nitrogen atom is a member of a heterocyclic ring, sulphamyl, alkylsulphamyl, preferably lower alkylsulphamyl, dialkylsulphamyl, preferably di(lower alkyl)sulphamyl, or said sulphamyl wherein the nitrogen is a member of a heterocyclic ring or $-SO_n$ alkyl, preferably lower alkyl, wherein $n$ is 0, 1 or 2, and 1 or 2 of the same or different substituents selected from the group consisting of alkyl, preferably lower alkyl, alkenyl, preferably lower alkenyl, alkoxy, preferably lower alkoxy, halogen, and trifluoromethyl; or
  e. a fused, saturated or unsaturated 5-, 6-, or 7- membered ring or said ring containing 1 or 2 oxygen or sulphur atoms;

As used hereinafter, the phrase, "compounds of the present invention", includes both the pyrazol-5-ones and their pharmaceutically acceptable, nontoxic salts.

If X in formula I contains an asymmetric carbon atom, then the compounds of the present invention may be isomers as well as racemates. The compounds of the present invention thus include all the optical isomers, as well as the racemates thereof.

In addition to the structure which is represented by formula I above, the compounds of the present invention may also be one of the following tautomeric forms or in the form of a mixture of such tautomers:

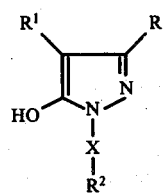

II

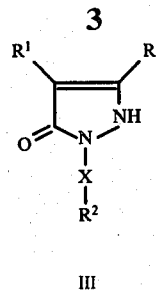

III

In addition, the 3-amino-pyrazol-5-ones according to the present invention may also be present in the following imino forms:

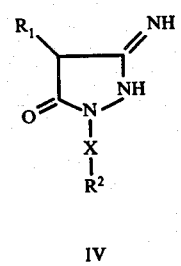

IV

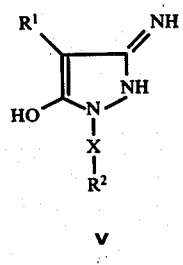

V

In formulas II, III, IV and V, R, R¹, R² are as above defined.

The compounds of the present invention may be produced according to the following processes:

A. A hydrazine of the formula
$$R^2-X-NH-NH_2 \quad VI$$

wherein R² and X are as above defined is reacted with an acetic acid derivative of the formula

VII wherein
R¹ is as above defined,
Y is hydroxy, alkoxy, preferably lower alkoxy, aralkoxy, preferably monoaryl-lower alkoxy, amino, or alkylamino, preferably lower alkylamino; and either
Y' is hydrogen and
Y'' is cyano, or —CH=O, or Y' and Y'' together form the moiety

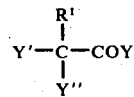

wherein Y''' is alkoxy, preferably lower alkoxy, aryloxy, preferably monoaryloxy, alkylmercapto, preferably lower alkylmercapto, aralkylmercapto, preferably monoaryl(lower alkyl)mercapto, or amino; either in the presence or the absence of an inert solvent and either in the presence or the absence of a basic or acidic catalyst such as an alkaline metal hydroxide, carbonate, or alkaline earth metal hydroxide or carbonate, or hydrogen halide acids, sulphuric acid or sulphonic acids at a temperature of from about 10° C to about 200° C;

B. reacting a compound of the formula:
$$R^2-X-A \quad VIII$$

wherein
R² and X are as above defined and A is a moiety capable of being cleaved during the course of the reaction, preferably halogen, dialkyloxonium, preferably di(lower alkyl)oxonium, dialkylsulphonium, preferably di(lower alkyl)sulphonium, trialkylammonium, preferably tri(lower alkyl)ammonium, arylsulphonic acid, preferably monoarylsulphonic acid, or trifluoromethylsulphonic acid, with a pyrazol-5-one of the formula

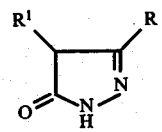
IX wherein R and R¹ are as above defined, either in the presence or the absence of an inert solvent, and either in the presence or the absence of an inorganic or organic base such as an alkali metal hydroxide, carbonate, alcoholate, hydride or amide, at a temperature of from about 10° C to about 200° C;

C. when R is amino, reacting a pyrazol-5-one of the formula

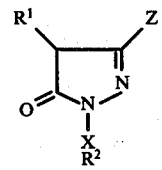
X wherein
R¹, R² and X are as above defined, and
Z is halogen, alkoxy, preferably lower alkoxy, aralkoxy, preferably monoaryl(lower alkoxy), alkylmercapto, preferably (lower alkyl)mercapto, or aralkylmercapto, preferably monoaryl(lower alkyl)mercapto, with ammonia, either in the presence or the absence of an inert solvent at a temperature of from about 20° C to about 220° C, preferably from about 50° C to about 150° C, either under atmospheric pressure or under elevated pressure;

D. when R is amino, reacting a pyrazol-5-one of the formula

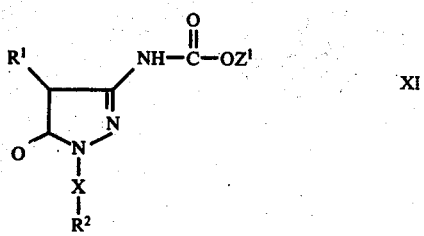

XI wherein

R¹, R² and X are as above defined, and

Z¹ is alkyl, preferably lower alkyl, aryl, preferably monoaryl, or aralkyl, preferably monoaryl(lower alkyl), under hydrolization conditions with an acid or base either in the presence or the absence of an inert solvent at a temperature of from about 20° C to about 200° C; or E. when R¹ is hydrogen reacting an acetylenecarboxylic acid of the formula

XII wherein

Z² is hydroxy, alkoxy, preferably lower lower alkoxy, aralkoxy, preferably monoaryl(lower alkoxy), amino or alkylamino, preferably (lower alkyl)amino, with a hydrazine of the formula

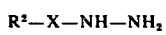

VI wherein

R² is as above defined either in the presence or the absence of an inert solvent at a temperature of from about 50° C to about 200° C.

The five processes A to E above set forth are hereinafter referred to as Process Variants A to E.

The optical isomers or enantiomers of the compounds according to the present invention can be separately prepared according to methods known from the literature (compare, for example, Houben Weyl, Methoden der organischen Chemie, IV/2, pages 509 et seq.) by interaction of the racemic forms of the compounds of the invention with a chiral medium, preferably by reaction of the racemate with the derivative of an optically active acid (for example, camphorsulphonic acid, bromocamphorsulphonic acid or quinic acid) or an optically active base (for example, brucine, morphone or strychnine). A mixture of diastereomeric reaction products is thus obtained which can be separated and prepared in a pure form with the aid of physico-chemical methods such as, for example, fractionation, and can subsequently be resolved into optically pure components.

Alternatively, the compounds of the present invention can be prepared in optically active form by producing them by one of the methods described above using optically active precursors. Thus:

a. an optically pure hydrazine of the formula VI (which can be prepared by known methods) can be reacted with an acetic acid derivative of the formula VII according to Process Variant A; or b. an optically pure pyrazol-5-one derivative of the formula X (which can be obtained by known methods) can be reacted with ammonia; or c. an optically pure pyrazol-5-one of the formula XI can be hydrolyzed; or d. an optically pure hydrazine of the formula VI can be reacted with an acetylene-carboxylic acid derivative of the formula XII.

The pyrazol-5-ones of formula I and their pharmaceutically acceptable, nontoxic salts can be interconverted according to manners per se known in the art.

Surprisingly, the new compounds of the invention display strong diuretic, saluretic, antithrombotic and antihypertensive actions. Hitherto, diuretic, saluretic, antithrombotic and antihypertensive actions have not been disclosed for the related pyrazol-5-one derivatives known from the prior art, so that the compounds according to the present invention both represent a novel class of compounds and in respect of these specific pharmaceutical actions can be regarded as an enrichment of pharmacy.

Depending on the nature of the starting compounds used, the synthesis of the compounds of the invention can be represented by the following illustrative equations, wherein 3-amino-4-methyl-1-(β-phenylmercapto-ethyl)-pyrazol-5-one, 4-methyl-1-(4-chlorobenzyl)-pyrazol-5-one, 4-methyl-1-(β-(3-chlorophenyl)-ethyl)-pyrazol-5-one, 3-amino-1-(β-phenylethyl)-pyrazol-5-one, 3-amino-1-(β-(3-chlorophenyl)-ethyl)pyrazol-5-one and 1-(4-chlorobenzyl)-pyrazol-5-one have been chosen as examples and the possible intermediate stages of the reaction sequence, products of which can sometimes be isolated, have not been shown.

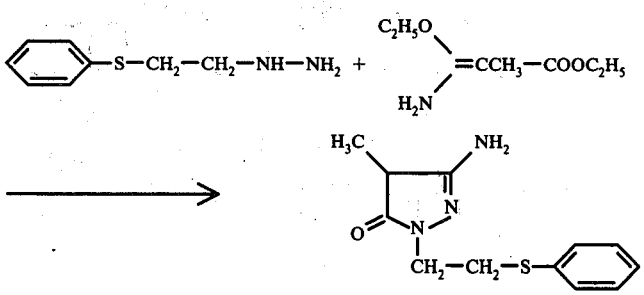

2. 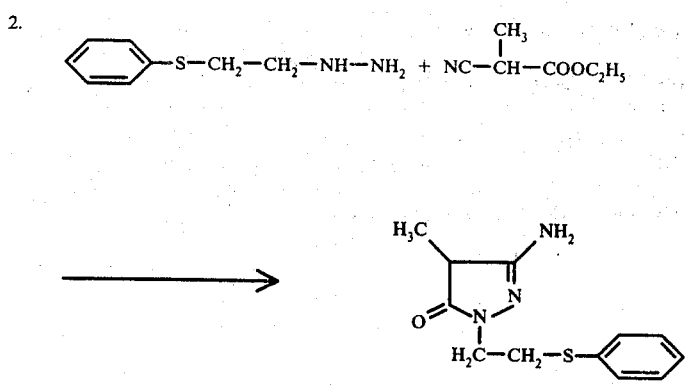
3. 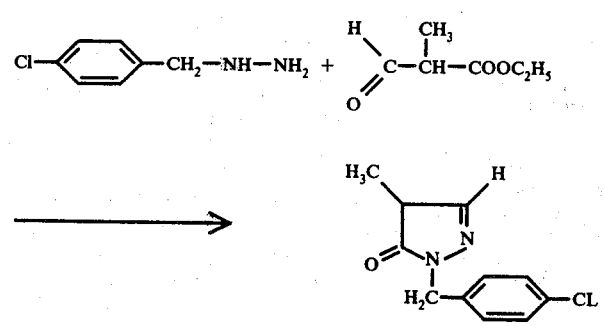
B) 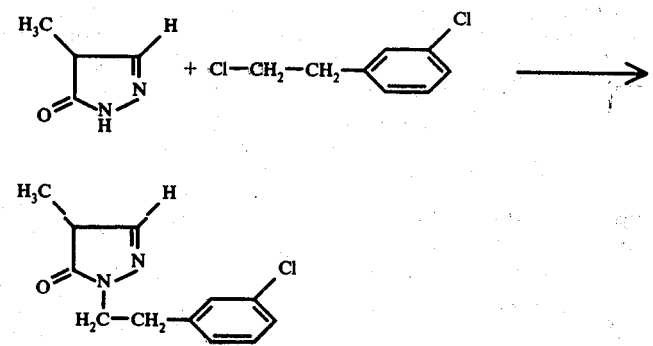
C) 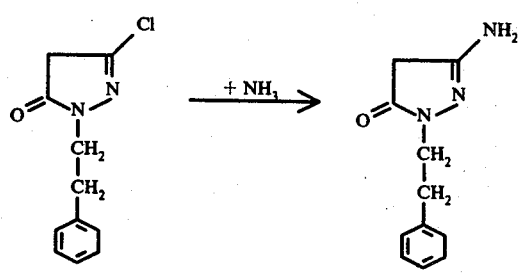

D) 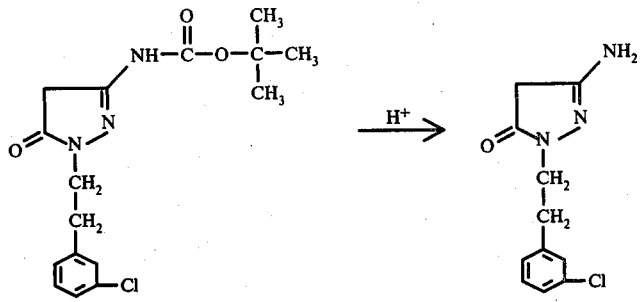

E) 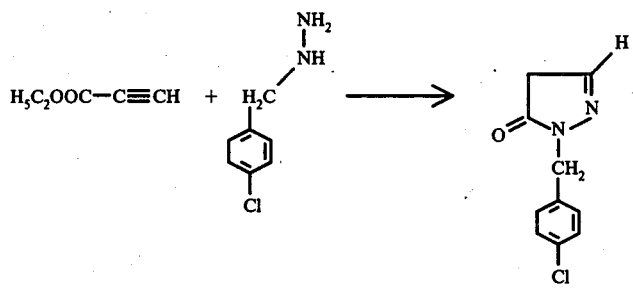

According to one embodiment of the present invention

R is hydrogen or amino;

R¹ is hydrogen, lower alkyl, lower alkenyl, monoaryl unsubstituted or substituted by lower alkoxy or aralkyl wherein the aryl moiety is a monoaryl moiety and the alkyl moiety is a lower alkyl moiety, said aralkyl being unsubstituted or substituted by lower alkoxy;

R² is aryl of 6 to 10 carbon atoms unsubstituted or substituted by:
  a. 1 or 2 of the same or different substituents selected from the group consisting of halogen, trifluoromethyl, alkyl of 1 to 8 carbon atoms, alkenyl of 2 to 8 carbon atoms and lower alkoxy;
  b. monoalkylamino of 1 to 4 carbon atoms in the alkyl moiety, dialkylamino of 1 to 4 carbon atoms in each alkyl moiety, cyano, trifluoromethoxy, nitro, alkylcarbamoyl of 1 to 4 carbon atoms in the alkyl moiety, di(lower alkyl)carbamoyl of 1 to 4 carbon atoms in each alkyl moiety, or said carbamoyl wherein the nitrogen atom is a member of a heterocyclic ring, sulphamyl, alkylsulphamyl of 1 to 4 carbon atoms in the alkyl moiety, dialkylsulphamyl of 1 to 4 carbon atoms in each alkyl moiety or said sulphamyl wherein the nitrogen atom is a member of a heterocyclic ring, or —SO$_n$ alkyl wherein $n$ is 0, 1 or 2 and the alkyl moiety has 1 to 4 carbon atoms;
  c. monoalkylamino of 1 to 4 carbon atoms in the alkyl moiety, dialkylamino of 1 to 4 carbon atoms in each alkyl moiety, cyano, trifluoromethoxy, nitro, alkylcarbamoyl of 1 to 4 carbon atoms in the alkyl moiety, di(lower alkyl)carbamoyl of 1 to 4 carbon atoms in each alkyl moiety, or said carbamoyl wherein the nitrogen atom is a member of a heterocyclic ring, sulphamyl, alkylsulphamyl of 1 to 4 carbon atoms in the alkyl moiety, dialkylsulphamyl of 1 to 4 carbon atoms in each alkyl moiety or said sulphamyl wherein the nitrogen atom is a member of a heterocyclic ring, or -SO$_n$ alkyl wherein n is 0, 1 or 2 and the alkyl moiety has 1 to 4 carbon atoms, and 1 or 2 of the same or different substituents selected from the group consisting of lower alkyl, lower alkenyl, lower alkoxy, halogen and trifluoromethyl; or
  d. a fused, saturated or unsaturated 5-, 6-, 7-membered ring or said ring containing 1 or 2 oxygen or sulphur atoms.

According to another embodiment of the present invention

R¹ is hydrogen, lower alkyl, lower alkenyl, phenyl unsubstituted or substituted by lower alkoxy or benzyl unsubstituted or substituted by lower alkoxy; and R² is aryl of 6 to 10 carbon atoms unsubstituted or substituted by:
  a. 1 or 2 of the same or different substituents selected from the group consisting of halogen, trifluoromethyl, alkyl of 1 to 4 carbon atoms, alkenyl of 2 to 4 carbon atoms and alkoxy of 1 to 4 carbon atoms;
  b. monoalkylamino of 1 to 4 carbon atoms in the alkyl moiety, dialkylamino of 1 to 4 carbon atoms in each alkyl moiety, cyano, trifluoromethoxy, nitro, alkylcarbamoyl of 1 to 4 carbon atoms in the alkyl moiety, di(lower alkyl)carbamoyl of 1 to 4 carbon atoms in each alkyl moiety, or said carbamoyl wherein the nitrogen atom is a member of a heterocyclic ring, sulphamyl, alkylsulphamyl of 1 to 4 carbon atoms in the alkyl moiety, dialkylsulphamyl of 1 to 4 carbon atoms in each alkyl moiety, or said sulphamyl wherein the nitrogen atom is a member of a heterocyclic ring, or —SO$_n$ alkyl wherein $n$ is 0, 1 or 2 and the alkyl moiety has 1 to 4 carbon atoms;
  c. monoalkylamino of 1 to 4 carbon atoms in the alkyl moiety, dialkylamino of 1 to 4 carbon atoms in each alkyl moiety, cyano, trifluoromethoxy, nitro, alkylcarbamoyl of 1 to 4 carbon atoms in the alkyl moiety, di(lower alkyl)carbamoyl of 1 to 4 carbon atoms in each alkyl moiety, or said carbamoyl wherein the nitrogen atom is a member of a heterocyclic ring, sulphamyl, alkylsulphamyl of 1 to 4 carbon atoms in the alkyl moiety, dialkylsulphamyl of 1 to 4 carbon atoms in each alkyl moiety or said sulphamyl wherein the nitrogen atom is a member of a heterocyclic ring, or —$SO_n$ alkyl wherein $n$ is 0, 1 or 2 and the alkyl moiety has 1 to 4 carbon atoms, and 1 or 2 of the same or different substituents selected from the group consisting of alkyl of 1 to 4 carbon atoms, alkenyl of 2 to 4 carbon atoms, alkoxy of 2 to 4 carbon atoms, halogen and trifluoromethyl; or d. a fused, saturated or unsaturated 5-, 6-, or 7- membered ring or said ring containing 1 or 2 oxygen or sulphur atoms.

According to another embodiment of the present invention $R^1$ is hydrogen, alkyl of 1 to 4 carbon atoms, alkenyl of 2 to 4 carbon atoms, phenyl unsubstituted or substituted by alkoxy of 1 to 4 carbon atoms or benzyl unsubstituted or substituted by alkoxy of 1 to 4 carbon atoms;

X is
a. ethylene, ethylene wherein 1 hydrogen atom on one of the carbon atoms is substituted by alkyl of 1 to 4 carbon atoms, ethylene wherein 1 hydrogen atom on each of the two carbon atoms is substituted by alkyl of 1 to 4 carbon atoms or said ethylene which is linked to $R^2$ via an oxygen or sulphur atom;
b. propenyl, propenyl wherein 1 hydrogen atom on one or two of the carbon atoms is substituted by alkyl of 1 to 4 carbon atoms, said propenyl being linked to the $N^1$ atom of the pyrazol ring via its methylene moiety; or
c. methylene;

provided that when X is methylene, $R^1$ is not hydrogen if R is amino;

$R^2$ is phenyl; naphthyl; or phenyl substituted by:
a. 1 or 2 straight or branched-chain alkyl moieties of 1 to 8 carbon atoms, or alkenyl moieties of 2 to 8 carbon atoms;
b. 1 or 2 alkoxy moieties of 1 to 6 carbon atoms;
c. cycloalkyl of 5, 6 or 7 carbon atoms or cycloalkenyl of 5, 6 or 7 carbon atoms;
d. 1 or 2 halogens;
e. 1 or 2 trifluoromethyl moieties;
f. trifluoromethoxy, nitro or cyano;
g. dialkylamino of 1 to 4 carbon atoms in each alkyl moiety;
h. alkylcarbamoyl, dialkylcarbamoyl, sulphamyl or dialkylsulphamyl, wherein alkyl is of 1 to 4 carbon atoms;
i. —$SO_n$ alkyl wherein n is 0 or 2 and alkyl is of 1 to 4 carbon atoms; or
j. a fused, saturated or unsaturated 5-, 6- or 7- membered isocyclic or heterocyclic ring or said ring having 1 sulphur atom or 1 or 2 oxygen atoms as ring members.

According to another embodiment of the present invention $R^1$ is hydrogen, alkyl of 1 to 4 carbon atoms, alkenyl of 2 to 4 carbon atoms, phenyl, benzyl, or phenyl or benzyl substituted by alkoxy of 1 or 2 carbon atoms;

X is
a. ethylene, ethylene wherein 1 hydrogen atom on one of the carbon atoms is substituted by alkyl of 1 to 4 carbon atoms, ethylene wherein 1 hydrogen atom on each of the two carbon atoms is substituted by alkyl of 1 to 4 carbon atoms or said ethylene which is linked to $R^2$ via an oxygen or sulphur atom;
b. propenyl, propenyl wherein 1 hydrogen atom on one or two of the carbon atoms is substituted by alkyl of 1 to 4 carbon atoms, said propenyl being linked to the $N^1$ atom of the pyrazol ring via its methylene moiety; or
c. methylene;

provided that when is methylene, $R^1$ is not hydrogen if R is amino;

$R^2$ is phenyl; naphthyl; or phenyl substituted by:
a. 1 or 2 straight or branched-chain alkyl moieties of 1 to 4 carbon atoms or alkenyl moieties of 2 to 4 carbon atoms;
b. 1 or 2 alkoxy moieties of 1 to 4 carbon atoms;
c. cycloalkyl of 5, 6 or 7 carbon atoms or cycloalkenyl of 5, 6 or 7 carbon atoms;
d. 1 or 2 fluoro, chloro or bromo moieties;
e. 1 or 2 trifluoromethyl moieties;
f. trifluoromethoxy, nitro or cyano;
g. dialkylamino of 1 or 2 carbon atoms;
h. alkylcarbamoyl, dialkylcarbamoyl, sulphamyl or dialkylsulphamyl, wherein alkyl is of 1 to 4 carbon atoms;
i. —$SO_n$ alkyl wherein n is 0 or 2 and alkyl is of 1 to 4 carbon atoms; or
j. a fused, saturated 5- or 6-membered ring.

According to another embodiment of the present invention $R^1$ is hydrogen, alkyl of 1 to 4 carbon atoms, alkenyl of 2 to 4 carbon atoms, phenyl or benzyl;

X is
a. ethylene, ethylene wherein 1 hydrogen atom on one of the carbon atoms is substituted by alkyl of 1 to 4 carbon atoms, ethylene wherein 1 hydrogen atom on each of the two carbon atoms is substituted by alkyl of 1 to 4 carbon atoms or said ethylene which is linked to $R^2$ via an oxygen or sulphur atom;
b. propenyl, propenyl wherein 1 hydrogen atom on 1 of the carbon atoms is substituted by alkyl of 1 to 4 carbon atoms, said propenyl being linked to the $N^1$ atom of the pyrazol ring via its methylene moiety; or
c. methylene;

provided that when X is methylene, $R^1$ is not hydrogen if R is amino;

$R^2$ is phenyl; naphthyl; or phenyl substituted by:
a. 1 or 2 members selected from the group consisting of straight or branched-chain alkyl and trifluoromethyl moieties of 1 to 4 carbon atoms;
b. alkoxy of 1 to 4 carbon atoms;
c. cycloalkyl of 5 or 6 carbon atoms;
d. 1 or 2 fluoro, chloro, bromo or iodo moieties;
e. chloro or bromo and alkyl of 1 or 2 carbon atoms, trifluoromethyl or sulphamyl;
f. trifluoromethoxy, nitro, cyclohexyl or dialkylamino of 1 or 2 carbon atoms;
g. carbamoyl or sulphamyl;
h. —$SO_n$ alkyl wherein $n$ is 0 or 2 and alkyl is of 1 to 4 carbon atoms; or
i. a fused, saturated, 5- or 6-membered ring.

According to another embodiment of the present invention
R¹ is hydrogen, methyl, ethyl, phenyl or benzyl;
X is
 a. ethylene, ethylene wherein 1 hydrogen atom on one of the carbon atoms is substituted by alkyl of 1 or 2 carbons, ethylene wherein 1 hydrogen atom on each of the two carbon atoms is substituted by alkyl of 1 or 2 carbon atoms, ethylene linked to R² via an oxygen atom or ethylene linked to R² via a sulphur atom;
 b. propenyl or propenyl wherein 1 hydrogen atom is substituted by alkyl of 1 or 2 carbon atoms, said propenyl being linked to the N¹ atom of the pyrazol ring via its methylene moiety; or
 c. methylene;
provided that when X is methylene, R¹ is not hydrogen if R is amino;
R² is phenyl; naphthyl; or phenyl substituted by fluorine, chlorine, bromine, iodine, trifluoromethyl, trifluoromethoxy, nitro, alkyl of 1 to 4 carbon atoms, sulphamyl, dimethylamino, alkoxy of 1 to 4 carbon atoms, cyclohexyl, dichlorine, chlorine and methyl, chlorine and bromine, chlorine and fluorine, chlorine and sulphamyl, chlorine and trifluoromethyl, dibromine, methyl and trifluoromethyl or by a fused, saturated, 5- or 6-membered ring.

According to another embodiment of the present invention
X is
 a. ethylene, ethylene where 1 hydrogen on 1 carbon atom is substituted by methyl or ethyl, ethylene wherein 1 hydrogen atom on each of the 2 carbon atoms is substituted by methyl, or ethylene linked to R² via an oxygen or sulphur atom;
 b. propenyl or propenyl wherein 1 hydrogen on 1 carbon atom is substituted by methyl, said propenyl being linked to the N¹ atom of the pyrazole ring via its methylene moiety; or
 c. methylene;
provided that when X is methylene, R¹ is not hydrogen if R is amino.

According to another embodiment of the present invention
R¹ is hydrogen, alkyl of 1 to 4 carbon atoms or phenyl;
X is
 a. ethylene, ethylene wherein 1 hydrogen atom of 1 carbon atom is substituted by methyl and linked to R² via an oxygen or sulphur atom or ethylene linked to R² via an oxygen or sulphur atom;
 b. propenyl; or
 c. methylene; provided that when X is methylene, R¹ is not hydrogen if R is amino;
R² is phenyl; naphthyl; or phenyl substituted by 1 or 2 chlorine, methyl, ethyl or trifluoromethyl moieties.

According to another embodiment of the present invention
R¹ is hydrogen, alkyl of 1 to 4 carbon atoms or phenyl;
X is
 a. ethylene, ethylene wherein 1 hydrogen atom of 1 carbon atom is substituted by methyl and linked to R² via an oxygen or sulphur atom or ethylene linked to R² via an oxygen or sulphur atom;

R² is naphthyl, phenyl or phenyl substituted by chlorine, methyl, trifluoromethyl, dichlorine, dimethyl, methyl and ethyl or methyl and trifluoromethyl.

According to Process Variant A
Y is preferably hydroxy, alkoxy of 1 to 6 carbon atoms, especially branched alkoxy of 3 to 6 carbon atoms and especially of 1 or 2 carbon atoms, benzyloxy, amino, or alkylamino or dialkylamino of 1 to 4 and especially 1 or 2 carbon atoms, and
Y' is hydrogen and
Y'' is cyano, or —CH=O; or
Y' and Y'' together form the moiety

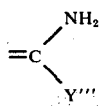

wherein Y''' is alkoxy of 1 to 6 carbon atoms, benzyloxy, phenoxy, benzylmercapto or amino; and
R² is preferably phenyl; naphthyl; or phenyl substituted by:
 a. 1 or 2 straight or branched-chain alkyl moieties of 1 to 8 carbon atoms, or alkenyl moieties of 2 to 8 carbon atoms;
 b. 1 or 2 alkoxy moieties of 1 to 6 carbon atoms;
 c. cycloalkyl of 5, 6 or 7 carbon atoms or cycloalkenyl of 5, 6 or 7 carbon atoms;
 d. 1 or 2 halogens;
 e. 1 or 2 trifluoromethyl moieties;
 f. trifluoromethoxy, nitro or cyano;
 g. dialkylamino of 1 to 4 carbon atoms in each alkyl moiety;
 h. alkylcarbamoyl, dialkylcarbamoyl, sulphamyl or dialkylsulphamyl wherein alkyl is of 1 to 4 carbon atoms;
 i. —SO$_n$ alkyl wherein $n$ is 0 or 2 and alkyl is of 1 to 4 carbon atoms; or
 j. a fused, saturated or unsaturated 5-, 6- or 7-membered isocyclic or heterocyclic ring or said ring having 1 sulphur atom or 1 or 2 oxygen atoms as ring members.

The hydrazines of formula VI which are used as starting materials according to Process Variant A are known in the literature or can be prepared by methods which are per se known. (Compare, for example, Houben-Weyl's *Methoden der organischen Chemie* (Methods of Organic Chemistry), Volume X, 2, page 6.)

Representative hydrazines of the formula VI include:
3-chlorobenzylhydrazine,
3-bromobenzylhydrazine,
4-chlorobenzylhydrazine,
4-bromobenzylhydrazine,
3,4-dichlorobenzylhydrazine,
3,4-dibromobenzylhydrazine,
4-chloro-3-bromobenzylhydrazine,
4-bromo-3-chlorobenzylhydrazine,
4-methylbenzylhydrazine,
3-methylbenzylhydrazine,
3-ethylbenzylhydrazine,
4-trifluoromethylbenzylhydrazine,
4-methyl-3-chlorobenzylhydrazine,
3-methyl-4-chlorobenzylhydrazine,
4-methyl-3-trifluoromethylbenzylhydrazine,
4-trifluoromethyl-3-chlorobenzylhydrazine,
4-chloro-3-trifluoromethylbenzylhydrazine, 4-sulphonamidobenzylhydrazine,
3-sulphonamido-4-chlorobenzylhydrazine,
4-methoxybenzylhydrazine,
5-hydrazinomethylindane,
2-hydrazinomethylnaphthalene,
2-hydrazinomethyl-5,6,7,8-tetrahydronaphthalene,
1-phenyl-3-hydrazino-prop-1-ene,
2-phenyl-4-hydrazino-but-2-ene,
1-phenyl-2-hydrazinomethyl-prop-1-ene,
1-phenyl-3-hydrazino-but-1-ene,
β-phenylethylhydrazine,
β-(3-chlorophenyl)-ethylhydrazine,
β-(3-bromophenyl)-ethylhydrazine,
β-(4-chlorophenyl)-ethylhydrazine,
β-(4-bromophenyl)-ethylhydrazine,
β-(3,4-dichlorophenyl)-ethylhydrazine,
β-(4-bromo-3-chlorophenyl)-ethylhydrazine,
β-(4-methylphenyl)-ethylhydrazine,
β-(4-trifluoromethylphenyl)-ethylhydrazine,
β-(3-chloro-4-methylphenyl)-ethylhydrazine,
[α-methyl-β-(3,4-dichlorophenyl)-ethyl]-hydrazine,
[α-methyl-β-(3-chloro-4-methylphenyl)-ethyl]-hydrazine,
[α-ethyl-β-(3,4-dichlorophenyl)-ethyl]-hydrazine,
[α-n-propyl-β-(3,4-dichlorophenyl)-ethyl]-hydrazine,
[β-methyl-β-(3,4-dichlorophenyl)-ethyl]-hydrazine,
[β-methyl-β-(3-chloro-4-methylphenyl)-ethyl]-hydrazine,
[β-propyl-β-(3,4-dichlorophenyl)-ethyl]-hydrazine,
β-phenoxy-ethylhydrazine,
β-(3-chlorophenoxy)-ethylhydrazine,
β-(3-chloro-4-methylphenoxy)-ethylhydrazine,
[β-methyl-β-(3,5-dichlorophenoxy)-ethyl]-hydrazine,
[(α-ethyl-β-phenoxy)-ethyl]-hydrazine and
β-phenylmercaptoethylhydrazine.

Acetic acid derivatives of the formula VII, which are used as starting materials, are known from the literature or can be prepared by processes known from the literature (compare Org. Synth., Coll. I, 249; Org. Synth., 41, 50; Cope, J. Amer. Chem. Soc., 67, 1047 (1947); C. C. Steele, J. Amer. Chem. Soc., 53, 286 (1931); A. H. Cook, J. Chem. Soc. (London) 1949, 3224).

Although referred to in this specification as acetic acid derivatives, the compounds of formula VII can perhaps more accurately be designated at β-aminoacrylic acid derivatives when Y' and Y" together form the moiety

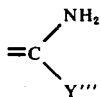

cyanoacetic acid derivatives when Y is hydrogen and Y" is cyano, or as formylcarboxylic acid derivatives when Y' is hydrogen and Y" is —COH.

Representative acetic acid derivatives of the formula VII include:
cyanoacetic acid methyl ester,
cyanoacetic acid ethyl ester,
cyanoacetic acid propyl ester,
cyanoacetic acid isopropyl ester,
cyanoacetic acid n-butyl ester (compare Org. Synth. 41, page 5),
cyanoacetic acid isobutyl ester,
cyanoacetic acid t.-butyl ester,
cyanoacetic acid hexyl ester,
cyanoacetic acid benzyl ester,
cyanoacetic acid amide,
cyanoacetic acid methylamide,
cyanoacetic acid diethylamide,
cyanoacetic acid butylamide,
α-cyanopropionic acid methyl ester,
α-cyanopropionic acid ethyl ester,
α-cyanopropionic acid propyl ester,
α-cyanopropionic acid isopropyl ester,
α-cyanopropionic acid n-butyl ester,
α-cyanopropionic acid isobutyl ester,
α-cyanopropionic acid t.-butyl ester,
α-cyanopropionic acid hexyl ester,
α-cyanopropionic acid benzyl ester,
α-cyanopropionic acid amide,
α-cyanopropionic acid methylamide,
α-cyanopropionic acid diethylamide,
α-cyanopropionic acid butylamide,
α-cyanobutyric acid ethyl ester,
α-cyanobutyric acid t.-butyl ester,
α-cyanobutyric acid diethylamide,
α-cyano-β-phenylpropionic acid ethyl ester,
β-amino-β-methoxyacrylic acid ethyl ester,
β-amino-β-ethyoxyacrylic acid ethyl ester,
β-amino-β-butoxyacrylic acid butyl ester,
β-amino-β-phenoxyacrylic acid ethyl ester,
β-amino-β-benzyloxyacrylic acid benzyl ester,
β-amino-βethoxyacrylic acid amide,
β-amino-βethoxyacrylic acid diethylamide,
β-amino-β-methylmercaptoacrylic acid ethyl ester,
β-amino-βbenzylmercaptoacrylic acid ethyl ester,
β-amino-βmethylmercaptoacrylic acid amide,
β,β-diaminoacrylic acid ethyl ester,
β,β-diaminoacrylic acid amide,
β-amino-β-methoxymethacrylic acid ethyl ester,
β-amino-β-ethoxymethacrylic acid ethyl ester,
β-amino-β-butoxymethacrylic acid butyl ester,
β-amino-β-phenoxymethacrylic acid ethyl ester,
β-amino-β-benzyloxymethacrylic acid ethyl ester,
β-amino-β-methylmercaptomethacrylic acid ethyl ester,
β-amino-β-benzylmercaptomethacrylic acid ethyl ester,
β-amino-β-ethoxymethacrylic acid amide,
β-amino-β-ethoxymethacrylic acid diethylamide,
β-amino-β-methylmercaptomethacrylic acid amide,
β,β-diaminomethacrylic acid ethyl ester,
β,β-diaminomethacrylic acid amide,
β-amino-β-ethoxy-α-ethylacrylic acid ethyl ester,
β-amino-β-methylmercapto-α-ethylacrylic acid ethyl ester,
β-amino-β-ethoxy-α-ethylacrylic acid amide,
β-amino-β-ethoxy-α-phenylacrylic acid ethyl ester,
β-amino-β-ethoxy-α-benzylacrylic acid ethyl ester,
α-formylacetic acid ethyl ester,
α-formylpropionic acid ethyl ester,
α-cyano-β-phenylpropionic acid ethyl ester and
α-cyano-phenylacetic acid ethyl ester.

Diluents for use according to Process Variant A include all inert organic solvents, which, when they are miscible with water, can also, if desired, be diluted with water. Preferred organic solvents include hydrocarbons (such as benzene, toluene and xylene), halogenated hydrocarbons (such as methylene chloride, chloroform, carbon tetrachloride and chlorobenzene), alcohols (such as methanol, ethanol, propanol, butanol, benzyl alcohol and glycol monomethyl ether), ethers (such as tetrahydrofuran, dioxane and glycol dimethyl ether), amides (such as dimethylformamide, dimethylacetamide, N-methylpyrrolidone and hexamethylphosphoric acid triamide), sulphoxides (such as dimethylsulphoxide), sulphones (such as sulpholane) and bases (such as pyridine, picoline, collidine, lutidine and quinoline).

As basic condensation agents in Process Variant A there may be used inorganic and organic bases. Preferred bases for this purpose include alkali metal hydroxides (such as sodium hydroxide and potassium carbonate) and alcoholates (such as sodium alcoholate and potassium alcoholate).

Alternatively there may be used as an acid catalyst, inorganic or organic acid. Preferred acids include hydrogen halide acids, sulphuric acid and sulphonic acids (such as toluenesulphonic acid and trifluoromethylsulphonic acid).

The reaction temperatures in Process Variant A can be varied over a substantial range. In general, the reaction is carried out at a temperature of from 10° C to about 200° C, preferably between 20° C and 100° C. It can be carried out under atmospheric pressure but also in closed vessels at a higher pressure.

In carrying out the process according to the invention, 1 mol of the hydrazine VI and 1 mol of β-aminoacrylic acid derivative VII (Y' and Y'' together are

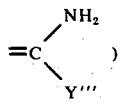

are reacted. It is possible to start either from the β-aminoacrylic acid derivative in the free form or from its acid addition salts. In the latter case it is desirable to add 1 mol of a base in order to liberate the β-aminoacrylic acid derivative. If the hydrazine derivative and the β-aminoacrylic acid derivative are employed in the free form, the addition of 1 to 10% of an acid catalyst is desirable. Another possible procedure is to add a correspondingly smaller amount of a base to the reaction mixture for the purpose of neutralizing the salt of β-aminoacrylic acid derivative. When using the acid addition salt, the reaction can also be carried out by isolating the intermediate amidrazone of the formula:

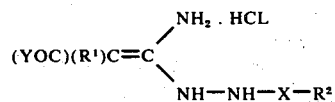

which are first produced and then cyclizing these in a second reaction step, thermally or by the action of a basic condensation agent, to give the compounds of the invention. However, the one-stage synthesis is particularly advantageous.

In carrying out the process according to the invention as illustrated in equation A 2), 1 mol of the cyanoacetic acid derivative VII (Y' is H, Y'' is cyano), and 1 to 3 mols, preferably 2 mols, of the basic condensation agent are employed per 1 mol of the hydrazine VI. With this procedure, the compounds of the present invention are obtained in the form of their salts and can be liberated by treatment with equivalent amounts of a dilute acid. They can easily be purified by recrystallization fron a suitable solvent or by dissolving them with dilute sodium hydroxide solution, filtering the solution in the presence of animal charcoal and precipitating the product by means of dilute acids.

If the process according to the present invention is carried out as illustrated in reaction scheme A 3), 1 mol of the hydrazine derivative VI is reacted with 1 mol of the α-formylcarboxylic acid derivative VII (Y' is hydrogen,

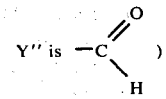

in a suitable diluent, the reaction mixture preferably being stirred for two hours at an elevated temperature after completion of the exothermic initial reaction. The compounds of the present invention, which in most cases are obtained in a crystalline form can easily be purified by recrystallization from a suitable solvent.

According to Process Variant B, A is preferably chlorine or bromine. The halogen compounds of formula VIII used in Process Variant B as starting substances are known from the literature or can be prepared by methods known from the literature (compare, for example, Houben-Weyl, Methoden der organischen Chemie (Methods of Organic Chemistry), Volume V, 3 (1962) and Volume V, 4 (1960)). The following halogen compounds VIII which are representative of the starting materials which can be used according to the present process include: 3-chlorobenzyl chloride,
  3-bromobenzyl chloride
  4-chlorobenzyl chloride,
  4-bromobenzyl chloride,
  3,4-dichlorobenzyl chloride,
  4-bromo-3-chlorobenzyl chloride,
  4-methylbenzyl chloride,
  4-trifluoromethylbenzyl chloride,
  3-chloro-4-methylbenzyl chloride,
  4-chlorobenzylbromide,
  3,4-dichlorobenzyl bromide,
  3-chloro-4-methylbenzyl bromide,
  γ-phenylallvl chloride,
  β-phenylethyl chloride,
  β-(3-chlorophenyl)-ethyl bromide,
  β-(3,4-dichlorophenyl)-ethyl chloride,
  β-(3-chloro-4-methylphenyl)-ethyl bromide,
  β-(3,4-dichlorophenyl)-n-propyl chloride,
  β-phenoxyethyl chloride,
  β-phenoxy-n-propyl chloride,
  β-phenoxy-n-butyl bromide,
  β-phenylmercaptoethyl chloride and
  β-phenylmercapto-n-butyl bromide.

The pyrazol-5-one derivatives of the formula IX used as starting compounds in Process Variant B are known from the literature or can be prepared by methods known from the literature (compare, for example, B. Graham et al., J. Amer. Chem. Soc., 71, 983 (1949); R. Jones et al. Tetrahedron, 19, 1947 (1963)).

Representative pyrazol-5-ones of forumla IX which can be used according to the process of the present invention include:
  3-amino-pyrazol-5-one,
  3-amino-4-methyl-pyrazol-5-one,
  3-amino-4-butylpyrazol-5-one, 3-amino-4-phenylpyrazol-5-one,
3-amino-4-benzylpyrazol-5-one,
4-methylpyrazol-5-one,
4-phenylpyrazol-5-one and
4-benzylpyrazol-5-one.

Possible diluents for use in Process Variant B are all inert solvents. Preferred solvents include hydrocarbons (such as benzene, toluene and xylene), alcohols (such as methanol, ethanol, propanol, butanol, benzyl alcohol and glycol monomethyl ether), ethers (such as tetrahydrofuran, dioxane and glycol dimethyl ether), amides (such as dimethylformamide and dimethylacetamide, N-methylpyrrolidone, and hexamethylphosphoric acid triamide), sulphoxides (such as dimethylsuphoxide) and sulphones (such as sulpholane).

Bases which can be used in Process Variant B include in principle, all inorganic and organic ides, carbonates, alcoholates, hydrides and amides.

The reaction temperatures in Process Variant B can be varied over a substantial range. Preferably, the reaction is carried out at a temperature of from 20° C to about 120° C. It is generally carried out under atmospheric pressure but one can also carry it out in a closed vessel at a higher pressure.

In carrying out Process Variant B, a salt is generally first prepared from one mol of the pyrazolone derivative IX in a suitable solvent by means of an equimolar amount of a base. One mol of the halogen compound is added to a solution of this salt and the entire reaction mixture is stirred, preferably at an elevated temperature.

The compounds of the present invention are preferably isolated by distilling of the solvent in vacuo, taking up the residue in water and rendering the aqueous mixture weakly acid. The compounds of the present invention obtained using this procedure can easily be purified by recrystallization from a suitable solvent.

According to Process Variant C, Z is preferably chlorine or bromine.

The pyrazol-5-one derivatives of formula X used as starting compounds in Process Variant C can be prepared in a simple manner by methods known from the literature (compare, for example, Japanese Patent 2872 ('64) (1961) and G. Barnikow, Chem. Ber., 100, 1661 (1967)).

The following pyrazole-5-ones of formula X, wherein Z is chlorine or bromine, are representative of those which can be used according to the process of the present invention:
3-chloro-4-methyl-1-(3-chlorobenzyl)-pyrazol-5-one,
3-chloro-4-methyl-1-(4-chlorobenzyl)-pyrazol-5-one,
3-chloro-4-methyl-1-(4-bromobenzyl)-pyrazol-5-one,
3-chloro-4-methyl-1-(3,4-dichlorobenzyl)-pyrazol-5-one,
3-bromo-4-methyl-1-(3,4-dichlorobenzyl)-pyrazol-5-one,
3-chloro-4-methyl-1-(4-bromo-3-chlorobenzyl)-pyrazol-5-one,
3-chloro-4-phenyl-1-(4-bromo-3-chlorobenzyl)-pyrazol-5-one,
3-chloro-4-methyl-1-(4-trifluoromethylbenzyl)-pyrazol-5-one,
3-chloro-4-methyl-1-(3-chloro-4-methylbenzyl)-pyrazol-5-one,
3-bromo-4-methyl-1-(3-chloro-4-methylbenzyl)-pyrazol-5-one,
3-chloro-4-benzyl-1-(3-chloro-4-methylbenzyl)-pyrazol-5-one,
3-chloro-1-(γ-phenylallyl)-pyrazol-5-one,
3-chloro-1-(β-phenylethyl)-pyrazol-5-one,
3-bromo-1-(β-phenylethyl)-pyrazol-5-one,
3-chloro-4-methyl-1-(β-phenylethyl)-pyrazol-5-one,
3-chloro-1-(β-[3-chlorophenyl]-ethyl)-pyrazol-5-one,
3-chloro-1-(β-[3,4-dichlorophenyl]-ethyl)-pyrazol-5-one,
3-chloro-1-(β-[3-chloro-4-methylphenyl]-ethyl)-pyrazol-5-one,
3-chloro-1-(β-phenoxyethyl)-pyrazol-5-one,
3-chloro-1-(β-phenoxy-n-propyl)-pyrazol-5-one and
3-chloro-1-(β-phenylmercaptoethyl)-pyrazol-5-one.

Possible diluents for use in Process Variant C are water and all inert organic solvents which, where they are water-miscible, can be diluted with water. Preferred organic solvents include hydrocarbons (such as benzene, toluene and xylene), alcohols (such as methanol, ethanol, propanol, butanol, benzyl alcohol and glycol monomethyl ether), and ethers (such as tetrahydrofuran, dioxane and glycol dimethyl ether).

The reaction temperatures in Process Variant C can be varied over a substantial range. The reaction is generally carried out at a temperature of from about 20° C to 220° C, but preferably between 50° C and 150° C. It can be carried out either under atmospheric pressure or in closed vessels at higher pressures.

In carrying out Process Variant C, one mol of the pyrazolone derivative X is generally reacted with a twofold to twenty-fold, preferably tenfold, excess of ammonia.

The procedure followed is preferably that the reactants, optionally in an inert solvent, are reacted in a closed vessel at an elevated temperature. The compounds of the present invention, thus obtained, can easily be purified by recrystallization from a suitable solvent.

According to Process Variant D, $Z^1$ is preferably straight or branched-chain alkyl of 1 to 6 carbon atoms, especially t-butyl, or a phenyl or benzyl. The pyrazol-5-one of the formula XI is hydrolyzed with an inorganic or organic acid such as a hydrogen halode acid, sulphuric acid, phosphoric acid, acetic acid, trifluoroacetic acid or a mixture of two or more thereof with a base such as an alkali metal hydroxide or alkali earth metal hydroxide as above described.

The pyrazol-5-one derivatives of the formula XI used as starting compounds have not hitherto been disclosed but can be prepared by methods known from the literature, for example, by reacting the carboxylic acid of the formula XIII, wherein $R^1$, $R^2$ and X are as above defined,

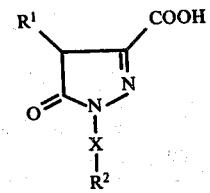

XIII which in turn can be obtained by hydrolysis of the corresponding esters which can be prepared from optionally substitued oxalacetic acid esters and hydrazines of the formula IV according to a modified Curtius reaction with diphenylphosphoryl azide (T. Shioiri et al., J. Amer. Chem. Soc., 94, 6203 (1972)) or by Weinstock's method (J. Org. Chem., 26, 3511 (1961)).

The following pyrazol-5-ones of the formula XI are representative of those which may be used according to the process of the present invention:

3-carbo-ethoxyamino-4-methyl-1-(3-chlorobenzyl)-pyrazol-5-one,
3-carboethoxyamino-4-methyl-1-(4-chlorobenzyl)-pyrazol-5-one,
3-carboethoxyamino-4-methyl-1-(4-bromobenzyl)-pyrazol-5-one,
3-carboethoxyamino-4-methyl-1-(3,4-dichlorobenzyl)-pyrazol-5-one,
3-carbo-t.-butoxyamino-4-methyl-1-(3,4-dichlorobenzyl)-pyrazol-5-one,
3-carbo-n-propoxyamino-4-methyl-1-(3,4-dichlorobenzyl)-pyrazol-5-one,
3-carboethoxyamino-4-methyl-1-(4-bromo-3-chlorobenzyl)-pyrazol-5-one,
3-carboethoxyamino-4-methyl-1-(4-trifluormethylbenzyl)-pyrazol-5-one,
3-carboethoxyamino-4-methyl-1-(3-chloro-4-methylbenzyl)-pyrazol-5-one,
3-carbo-t.-butoxyamino-4-methyl-1-(3-chloro-4-methylbenzyl)-pyrazol-5-one,
3-carboethoxyamino-4-phenyl-1-(3-chloro-4-methylbenzyl)-pyrazol-5-one,
3-carboethoxyamino-4-benzyl-1-(3-chloro-4-methylbenzyl)-pyrazol-5-one,
3-carboethoxyamino-1-($\gamma$-phenylallyl)-pyrazol-5-one,
3-carboethoxyamino-1-($\beta$-phenylethyl)-pyrazol-5-one,
3-carbo-t.-butoxyamino-1-($\beta$-phenylethyl)-pyrazol-5-one,
3-carbobenzyloxyamino-1-($\beta$-phenylethyl)-pyrazol-5-one,
3-carbophenoxyamino-1-($\beta$-phenylethyl)-pyrazol-5-one,
3-carbo-t.-butoxyamino-1-($\beta$-[3-chlorophenyl]-ethyl)-pyrazol-5-one,
3-carbo-t.-butoxyamino-1-($\beta$-[3,4-dichlorophenyl]-ethyl)-pyrazol-5-one,
3-carbo-t.-butoxyamino-1-($\beta$-[3-chloro-4-methylphenyl]-ethyl)-pyrazol-5-one,
3-carbo-t.-butoxyamino-1-($\beta$-phenoxyethyl)-pyrazol-5-one,
3-carbo-t.-butoxyamino-1-($\beta$-phenoxy-n-propyl)-pyrazol-5-one and
3-carbo-t.-butoxyamino-1-($\beta$-phenylmercaptoethyl)-pyrazol-5-one.

Possible diluents for use in Process Variant D are water and water-miscible inert organic solvents. Preferred solvents include alcohols (such as methanol, ethanol, propanol, ethylene glycol and glycol monomethyl ether), and ethers (such as tetrahydrofuran or dioxane).

The reaction temperatures in Process Variant D can be varied over a substantial range. Preferably, the reaction is carried out at a temperature of from about 70° C to about 150° C. Normally the reaction is carried out under atmospheric pressure, but it can also be carried out in closed vessels at higher pressure.

In carrying out Process Variant D, an aliquot part of the pyrazolone derivative XI, optionally in an inert solvent, is generally stirred with, preferably, a fivefold to 25 fold excess of an aqueous solution of an acid or a base at an elevated temperature. The compounds of the present invention precipitate after neutralization of the reaction solution and can easily be purified by recrystallization from a suitable solvent.

According to Process Variant E, $Z^2$ is preferably hydroxy, straight or branched-chain alkoxy of 1 to 6 carbon atoms, especially methoxy or ethoxy, benzyloxy or amino or alkylamino or dialkylamino of 1 to 4 carbon atoms in each alkyl moiety.

The acetylenecarboxylic acid derivatives of the formula XII used as starting compounds in Process Variant E are known from the literature or can be prepared by methods known from the literature. (Compare, for example, Beilstein's *Handbuch der organischen Chemie* (Handbook of Organic Chemistry) 2, III, 1,477 et seq. (1961) and 9, III, 3,061 et seq (1971)).

Representative acetylenecarboxylic acids of the formula XII which may be used according to the process of the present invention include:

propiolic acid ethyl ester,
propiolic acid n-butyl ester,
propiolic acid isopropyl ester,
propiolic acid benzyl ester,
propiolic acid amide,
propiolic acid dimethylamide,
propiolic acid ethylamide,
propiolic acid n-butylamide and
propiolic acid diethylamide.

The hydrazines VI used in Process Variant E are the same as those used in Process Variant A, q.v.

Possible diluents for use in Process Variant E are all inert organic solvents which, where they are watermiscible, can be diluted with water. Preferred organic solvents include hydrocarbons (such as benzene, toluene and xylene), halogenated hydrocarbons (such as methylene chloride, chloroform, carbon tetrachloride and chlorobenzene), alcohols (such as methanol, ethanol, propanol, butanol, benzyl alcohol and glycol monomethyl ether), ethers (such as tetrahydrofuran, dioxane and glycol dimethyl ether), amides (such as dimethylformamide, dimethylacetamide, N-methylpyrrolidone and hexamethylphosphoric acid triamide), sulphoxides (such as dimethylsulphoxide), sulphones (such as sulpholane) and bases (such as pyridine, picoline, collidine, lutidine and quinoline).

The reaction temperatures in Process Variant E can be varied within a substantial range. In general, the reaction is carried out at a temperature of from about 50° C to about 200° C, preferably between 70° C and 150° C. It is carried out under atmospheric pressure but can also be carried out in closed vessels at a higher pressure.

In carrying out Process Variant E, 1 mol of the acetylenecarboxylic acid derivative XII, optionally in a suitable diluent, is generally reacted with 1 mol of the hydrazine VI. The compounds of the present invention, which, in most cases, are obtained in a crystalline form, if necessary after evaporating off the diluent, can easily be purified by recrystallization from a suitable solvent.

The quantities mentioned in Process Variants A to E can, of course, be varied slightly.

The following compounds are representative of those of the present invention:

1-(β-3-methylphenylmercapto)-ethyl)-pyrazol-5-one,
1-(β-phenethyl)-pyrazol-5-one,
4-methyl-1-(β-phenoxyethyl)-pyrazol-5-one,
4-methyl-1-(β-(3-chlorophenoxy)-ethyl)-pyrazol-5-one,
4-methyl-1-(β-(3-methylphenoxy)-ethyl)-pyrazol-5-one,
4-methyl-1-(β-(3,4-dichlorophenoxy)-ethyl)-pyrazol-5-one,
4-methyl-1-(β-(3,5-dichlorophenoxy)-ethyl)-pyrazol-5-one,
4-methyl-1-(β-(3-trifluoromethoxyphenoxy)-ethyl)-pyrazol-5-one,
4-methyl-1-(β-(3-ethylphenoxy)-ethyl)-pyrazol-5-one,
4-ethyl-1-(3,4-dichlorobenzyl)-pyrazol-5-one,
4-ethyl-1-(β-(3-chlorophenoxy)-ethyl)-pyrazol-5-one,
4-phenyl-1-(3,4-dichlorobenzyl)-pyrazol-5-one,
4-phenyl-1-(β-phenoxyethyl)-pyrazol-5-one,
4-phenyl-1-(β-(3-chlorophenoxy)-ethyl)-pyrazol-5-one,
4-benzyl-1-(3-chlorobenzyl)-pyrazol-5-one,
4-benzyl-1-(4-chlorobenzyl)-pyrazol-5-one,
4-benzyl-1-(β-phenoxyethyl)-pyrazol-5-one,
4-methyl-1-(γ-(3-chlorophenyl)-allyl)-pyrazol-5-one,
4-methyl-1-(α-methyl-γ-phenylallyl)-pyrazol-5-one,
3-amino-1-(γ-(3,4-dichlorophenyl)-allyl)-pyrazol-5-one,
3-amino-1-(β-methyl-γ-phenyl)-allyl)-pyrazol-5-one,
4-methyl-1-(3-chloro-4-methylbenzyl)-pyrazol-5-one,
3-amino-1-(β-(2-methylphenoxy)-ethyl)-pyrazol-5-one,
3-amino-1-(β-(2-chlorophenxoy)-ethyl)-pyrazol-5-one,
3-amino-1-(α-methyl-β-phenoxyethyl)-pyrazol-5-one,
3-amino-1-(α-methyl-β-(3-chloro-4-methylphenoxy)-ethyl)-pyrazol-5-one,
3-amino-1-(β-methyl-β-(4-cyclohexylphenoxy)-ethyl)-pyrazol-5-one,
3-amino-1-(β-(2-nitrophenoxy)-ethyl)-pyrazol-5-one,
3-amino-1-(β-ethyl-β-(4-isopropylphenoxy)-ethyl)-pyrazol-5-one,
3-amino-1-(β-(naphthyl-(2)-oxy)-ethyl)-pyrazol-5-one,
3-amino-1-(β-methyl-β-(4-methylphenylmercapto)-ethyl)-pyrazol-5-one,
3-amino-1-(β-(naphthyl-(2)-mercapto)-ethyl)-pyrazol-5-one,
3-amino-1-(β-(3,4-trimethylenephenyl)-ethyl)-pyrazol-5-one,
3-amino-1-(β-(4-chlorophenyl)-ethyl)-pyrazol-5-one,
3-amino-1-(α,β-dimethyl-β-phenylethyl)-pyrazol-5-one,
3-amino-1-(β-methyl-β-(3-chloro-4-methylphenyl)-ethyl)-pyrazol-5-one,
3-amino-1-(α-ethyl-β-phenylethyl)-pyrazol-5-one,
3-amino-4-methyl-1-(3-chlorobenzyl)-pyrazol-5-one,
3-amino-4-methyl-1-(3-bromobenzyl)-pyrazol-5-one,
3-amino-4-methyl-1-(4-bromobenzyl)-pyrazol-5-one,
3-amino-4-methyl-1-(3-fluorobenzyl)-pyrazol-5-one,
3-amino-4-methyl-1-(4-fluorobenzyl)-pyrazol-5-one,
3-amino-4-methyl-1-(4-iodobenzyl)-pyrazol-5-one,
3-amino-4-methyl-1-(4-chloro-3-bromobenzyl)-pyrazol-5-one,
3-amino-4-methyl-1-(4-bromo-3-chlorobenzyl)-pyrazol-5-one,
3-amino-4-methyl-1-(4-fluoro-3-chlorobenzyl)-pyrazol-5-one,
3-amino-4-methyl-1-(3,4-dibromobenzyl)-pyrazol-5-one,
3-amino-4-methyl-1-(4-methylbenzyl)-pyrazol-5-one,
3-amino-4-methyl-1-(4-isopropyl)-pyrazol-5-one,
3-amino-4-methyl-1-(4-n-butylbenzyl)-pyrazol-5-one,
3-amino-4-methyl-1-(4-cyclohexylbenzyl)-pyrazol-5-one,
3-amino-4-methyl-1-(4-trifluoromethylbenzyl)-pyrazol-5-one,
3-amino-4-methyl-1-(4-methyl-3-chlorobenzyl)-pyrazol-5-one,
3-amino-4-methyl-1-(3-methyl-4-chlorobenzyl)-pyrazol-5-one,
3-amino-4-methyl-1-(4-trifluoromethyl-3-chlorobenzyl)-pyrazol-5-one,
3-amino-4-methyl-1-(4-methyl-3-trifluoromethylbenzyl)-pyrazol-5-one,
3-amino-4-methyl-1-(4-chloro-3-trifluoromethylbenzyl)-pyrazol-5-one,
3-amino-4-methyl-1-(4-nitrobenzyl)-pyrazol-5-one,
3-amino-4-methyl-1-(4-sulphonamidobenzyl)-pyrazol-5-one,
3-amino-4-methyl-1-(3-sulphonamido-4-chlorobenzyl)-pyrazol-5-one,
3-amino-4-methyl-1-(4-methoxybenzyl)-pyrazol-5-one,
3-amino-4-methyl-1-(4-isopropyloxybenzyl)-pyrazol-5-one,
3-amino-4-methyl-1-(4-trifluoromethoxybenzyl)-pyrazol-5-one,
3-amino-4-methyl-1-(4-dimethylaminobenzyl)-pyrazol-5-one,
3-amino-4-methyl-1-(3,4-trimethylenebenzyl)-pyrazol-5-one,
3-amino-4-methyl-1-(3,4-tetramethylenebenzyl)-pyrazol-5-one,
3-amino-4-methyl-1-(α-benzyl-n-propyl)-pyrazol-5-one,
3-amino-4-methyl-1-(α,β-dimethyl-β-phenylethyl)-pyrazol-5-one,
3-amino-4-methyl-1-(β-methyl-β-phenoxyethyl)-pyrazol-5-one and,
3-amino-4-methyl-1-(β-(naphthyl-(2)-oxy)-ethyl)-pyrazol-5-one.

The compounds of the present invention are particularly useful for oral or parenteral administration in effecting diuresis and saluresis and can therefore be used for the treatment of oedematous and hypertonic conditions and for flushing out toxic substances.

Representative pyrazol-5-ones of the present invention were tested and the following data is representative of the diuretic and saluretic activity of the compounds of the present invention.

Diuresis experiment with dogs a. Method

Beagle bitches were used.

On the day of the experiment, the animals were given 1 ml/kg of a solution which contained 0.4% of NaCl and 0.2% of KCl every 30 minutes by means of a probang. Thereafter, the test preparation was administered orally and the change in excretion of electrolyte was measured in the urine in comparison with control groups. The amounts of urine were converted to ml/kg. It was then possible to calculate the excretion in $\mu$ equivalents/kg from the volume of urine and the measured electrolyte concentration. Sodium and potassium were determined by flame photometry.

b. Results

The results are shown in Table I. The renal excretion of sodium and water was increased substantially after oral administration of the test preparation. The effect depended on the dose.

Table I

| | | Excretion in µequivalent or ml/kg/1 hour | | |
|---|---|---|---|---|
| | Control | Na$^+$ 140 | K$^+$ 152 | H$_2$O 2.0 |
| 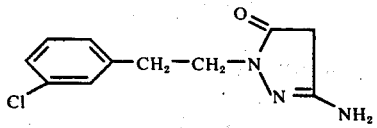 | 3 mg/kg | 326 | 290 | 2.6 |
| 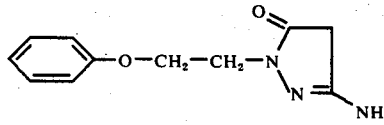 | 3 mg/kg | 1.637 | 218 | 14.9 |
| 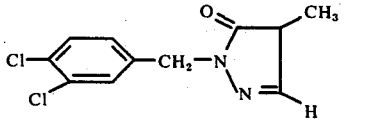 | 3 mg/kg | 637 | 319 | 5.7 |

The pharmaceutical compositions of the present invention contain a major or minor amount, e.g., 0.1 to 99.5%, preferably 0.5 to 90%, of active ingredient as above defined in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage for parenteral administration will be from 0.01 to 50, and preferably 0.1 to 10 mg/kg of body weight per day, whereas the oral dosage will be 0.1 to 500, and preferably 0.5 to 100 mg/kg of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitable comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the graulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended fo subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

The preferred daily dose for parenteral administration is 0.5 mg to 50g, particular 5 mg to 1 g, of active agent; for oral administration the preferred daily dosage of active agent is 5 mg to 50 g, particularly 25 mg to 10 g.

While the routes of administration include oral parenteral (i.e., intramuscular, intraperitoneal, and intravenous), and rectal, oral administration and parenteral administration are particularly preferred.

The preferred pharmaceutical compositions are therefore those in a form suitable for oral administration such as tablets and suspensions and those suitable for parenteral administration such as solutions and suspensions.

Examples A and B set forth below are illustrative of pharmaceutical compositions embodying the compounds of the present invention:

EXAMPLE A 200 g of 3-amino-4-methyl-1-(3-chlorobenzyl)-pyrazol-5-one are comminuted to a powder and mixed with 300 g of lactose and 200 g of potato starch, and after moistening with an aqueous gelatine solution the mixture is granulated through a sieve. After drying, 60 g of talc and 5 g of sodium lauryl sulphate are added and 10,000 tablets each containing 20 mg of active compound are pressed from the mixture.

EXAMPLE B 20 g of the sodium salt of 3-amino-4-methyl-1-(4-chlorobenzyl)-pyrazol-5-one are dissolved in 1,000 ml of propylene glycol and the solution is made up to 2,000 ml with water. This solution is filled under aseptic conditions into sterile ampoules each of 5 ml capacity and each containing 50 mg of active compound.

The following Preparative Examples describe by way of illustration only the production of certain compounds of the invention using the process of the invention.

EXAMPLE 1

(4-Methyl-1-(3,4-dichlorobenzyl)-pyrazol-5-one, by Process Variant A).

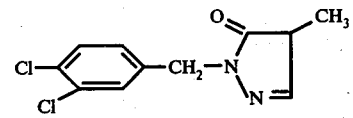

10.9 g of 3,4-dichlorobenzylhydrazine were added dropwise to a solution of 7.5 g of α-formylpropionic acid ethyl ester in 50 ml of ethanol. After stirring overnight at room temperature, the solvent was distilled off in vacuo and the solid residue was recrystallized from ethanol.

Melting point 156° C; yield 9.3 g (64%).

EXAMPLE 2

(4-Methyl-1-(3,4-dichlorobenzyl)-pyrazol-5-one, by Process Variant B).

19.6 g of 4-methylpyrazol-5-one were added in portions to a suspension of 5.0 g of sodium hydride in 100 ml of absolute dimethylformamide. After the evolution of $H_2$ had ceased, 39 g of 3,4-dichlorobenzyl chloride were added dropwise to the reaction solution.

The mixture was then stirred for 2 hours at 60° C, the solvent was distilled off in vacuo, the residue was taken up in water and the mixture was acidified with dilute acetic acid. The crude product thereby obtained was recrystallized from ethanol.

Melting point 155°–157° C; yield 13 g (25%)

EXAMPLE 3

(3-Amino-1-(β-phenyl-ethyl)-pyrazol-4-one).

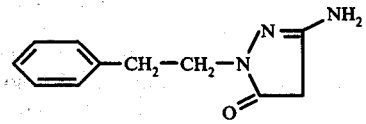

A pinch of p-toluenesulphonic acid was added to 23.7 g of β-amino-β-ethoxyacrylic acid ethyl ester in 150 ml of tetrahydrofuran and 20.4 g of phenylethylhydrazine were then added under nitrogen.

The reaction mixture was stirred overnight under $N_2$ at 40° C and was then concentrated in vacuo. The oily residue was dissolved in a little 2 N sodium hydroxide solution. Any starting material still present, and by-products, were extracted from the aqueous phase with ether.

The aqueous phase was clarified with charcoal, acidified with acetic acid (pH 5) and thoroughly shaken with methylene chloride. The methylene chloride phase was dried with sodium sulphate and concentrated, giving a crystalline product which was recrystallized from ethanol.

Melting point 162°–164° C; yield 14 g (42%)

The compounds shown in the table which follows were obtained analogously to Example 3;

EXAMPLE 8

(3-Amino-1-(α-methyl-β-(2-chlorophenoxy)-ethyl)-pyrazol-5-one)

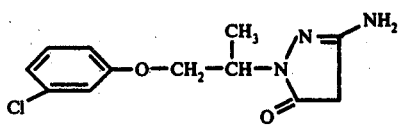

A mixture of 31.8 g of β-amino-β-ethoxyacrylic acid ethyl ester, 150 ml of absolute ethanol, 42 g of α-methyl-β-(3-chlorophenoxy)-ethylhydrazine and a pinch of p.-toluene-sulphonic acid was stirred overnight under nitrogen at room temperature and then concentrated in vacuo. The residue was triturated with a little ether. Hereupon, the crude solid crystallized out. It was recrystallized from methanol.

| No. | Structural formula | Recrystallization from | Yield, % of theory | Melting point ° C |
|---|---|---|---|---|
| 4 | F₃C—⌬—CH₂—CH₂—N... NH₂ (pyrazolone)  From: 3-trifluorophenylethylhydrazine + (x)* | Ethanol | 71.5 | 77–79 |
| 5 | Cl—⌬—CH₂—CH₂—N... NH₂ (pyrazolone)  From 3-chlorophenylethylhydrazine + (x)* | Ethanol | 65 | 126–128 |
| 6 | CH₃—⌬—CH₂—CH₂—N... NH₂ (pyrazolone)  From 4-methylphenylethylhydrazine + (x)* | Ethanol | 69 | 127–129 |
| 7 | ⌬—CH=CH—CH₂—N... NH₂ (pyrazolone)  From: γ-phenyl-allylhydrazine + (x)* | Methanol | 48 | 130–132 |

(x)* = β-amino-β-ethoxyacrylic acid ethylester

Melting point 158°–160° C; yield 23 g (43%)

The compounds shown in the table which follows were obtained analogously to Example 8:

| No. | Structural formula | Recrystallization from | Yield, % of theory | Melting Point ° C |
|---|---|---|---|---|
| 9 | ⌬—O—CH₂—CH₂—N... NH₂ (pyrazolone)  From: phenoxy-ethylhydrazine + (x)* | Ethanol | 51 | 130–132 |
| 10 | H₃C—⌬(CH₃)—O—CH₂—CH₂—N... NH₂ (pyrazolone) | Ethanol | 46.5 | 124–126 |

-continued

| No. | Structural formula | Recrystallization from | Yield, % of theory | Melting Point °C |
|---|---|---|---|---|
| | From: 3,4-di-methylphenoxy-ethylhydrazine + (x)* | | | |
| 11 | [structure: 3,4-dimethylphenoxy-ethyl-pyrazolone with NH₂] From: 3-methyl-5-ethylphenoxy-ethylhydrazine + (x)* | Ethanol | 54 | 91–93 |
| 12 | [structure: 3-methylphenoxy-ethyl-pyrazolone with NH₂] From: 3-methylphenoxy-ethylhydrazine + (x)* | Methanol | 44 | 124–126 |
| 13 | [structure: 4-methylphenoxy-ethyl-pyrazolone with NH₂] From: 4-methylphenoxy-ethylhydrazine + (x)* | Methanol | 61 | 149–151 |
| 14 | [structure: 4-chlorophenylthio-ethyl-pyrazolone with NH₂] From: 4-chlorophenylthio-ethylhydrazine + (x)* | Methanol | 55 | 115–117 |
| 15 | [structure: phenylthio-ethyl-pyrazolone with NH₂] From: phenylthio-ethylhydrazine + (x)* | Ethanol | 51 | 100–102 |

(x)* = β-amino-β-ethoxyacrylic acid ethyl ester

EXAMPLE 16

(same compound as Example 12; Process Variant A)

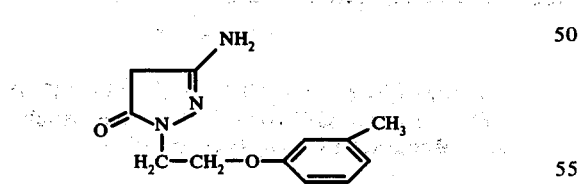

A mixture of 22.6 g of cyanoacetic acid ethyl ester and 33.2 g of β-(3-methylphenoxy)-ethylhydrazine in 100 ml of ethanol was added to a solution of 9.2 g of sodium in 200 ml of ethanol at room temperature. The reaction mixture was then warmed to 60° C for 2 hours, the solvent was distilled off in vacuo and the residue was taken up in water. After extraction with ether, the aqueous phase was acidified with dilute acetic acid, whereupon the crude product precipitated. This was twice recrystallized from ethanol.

Melting point 124°–126° C; yield 15 g (32%)

EXAMPLE 17

(3-Amino-4-methyl-1-(4-chlorobenzyl)-pyrazol-5-one).

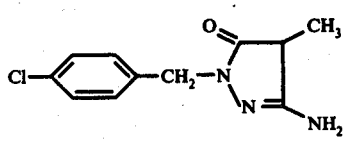

31.2 g of p.-chlorobenzylhydrazine were added dropwise under nitrogen to a solution of 34.6 of β-amino-β-ethoxymethacrylic acid ethyl ester and a pinch of p.-toluenesulphonic acid in 200 ml of ethanol, whereupon the temperature rose from 21° C to 31° C. After standing overnight, the product which had precipitated was filtered off and recrystallized from ethanol.

Melting point 174° C; yield 22 g (46%)

The compounds shown in the table which follows were prepared analogously to the procedure described in Example 17:

| No. | Structural formula | Recrystallization from | Yield, % of theory | Melting point ° C |
|---|---|---|---|---|
| 18 | ![structure] From: 3,4-di-chlorobenzylhydrazine + (y)* | Ethanol | 54 | 147 |
| 19 | ![structure] From: thyl-methylhydrazine + (y)* | Ethanol | 43 | 120 |
| 20 | ![structure] From: phenoxyethylhydrazine + (y)* | Ethanol | 40 | 126 |

(y)* = β-amino-β-ethoxy-methacrylic acid ethyl ester

EXAMPLE 21

(same compound as Example 17; Process Variant A)

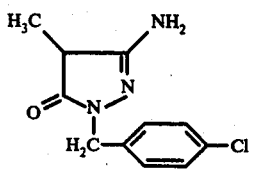

A mixture of 25.4 g of α-cyanopropionic acid ethyl ester and 31.2 g of 4-chlorobenzylhydrazine in 100 ml of ethanol was added to a solution of 9.2 g of sodium in 200 ml of ethanol at room temperature. The reaction mixture was then warmed to 60° C for 2 hours, the solvent was distilled off in vacuo and the residue was taken up in water. After extraction with ether, the aqueous phase was acidified with dilute acetic acid and the crude product which precipitated was twice recrystallized from ethanol.

Melting point 172°–174° C; yield 12 g (25%)

EXAMPLE 22

(3-Amino-4-n.-butyl-1-(3,4-dichlorobenzyl)-pyrazol-5-one)

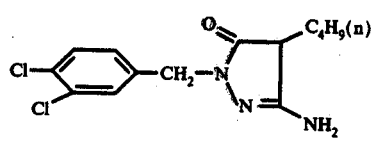

36.5 g of 3,4-dichlorobenzylhydrazine were added dropwise under nitrogen to a solution of 41.1 g of α-n.-butyl-β-amino-β-ethoxyacrylic acid ethyl ester and a pinch of p-toluenesulphonic acid in 100 ml of ethanol. After stirring for a further 2 hours, the mixture was left to stand overnight. The solvent was distilled off and a 1:1 mixture of ether and petroleum ether was added to the residue, whereupon the product crystallized through.

Melting point 102° C; yield 22 g (37%)

The compounds shown in the table which follows were obtained analogously to Example 22:

| No. | Structural formula | Recrystallization from | Yield, % of theory | Melting point ° C |
|---|---|---|---|---|
| 23 | ![structure] From: phenoxyethylhydrazine + (z)* | Ethanol | 32 | 109 |

| No. | Structural formula | Recrystallization from | Yield, % of theory | Melting point °C |
|---|---|---|---|---|
| 24 | 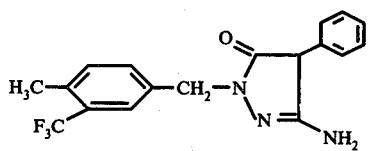 | Ethanol | 17 | 154 |

From: 3,4-di-chlorobenzylhydrazine + (z)*

(z)* = α-sec.-butyl-β-amino-β-ethoxyacrylic acid ethyl ester

EXAMPLE 25

(3-Amino-4-phenyl-1-(3-trifluoromethyl-4-methylbenzyl)-pyrazol-5-one).

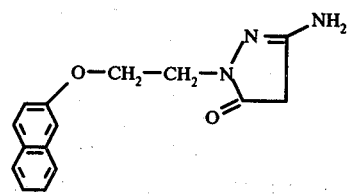

31.5 g of 3-trifluoromethyl-4-methylbenzylhydrazine were added dropwise under nitrogen to a solution of 35.3 g of α-phenyl-β-amino-β-ethoxyacrylic acid ethyl ester and 1 g of p-toluenesulphonic acid in 150 ml of ethanol. After stirring overnight, the solvent was distilled off in vacuo and the residue was recrystallized from dimethylformamide.

Melting point 211° C; yield 22 g (42%)

The compound shown in the table which follows was obtained analogously to Example 25:

whereupon the reaction product crystallized out. It was recrystallized from ethanol.

Melting point 146°-148° C. Yield 7.5 g (35% of theory).

EXAMPLE 28

(3-Amino-1-(β-(naphthyl-(2)-oxy)-ethyl)-pyrazol-5-one)

40 ml of glacial acetic acid were added to 0.1 mol of 1-(β-(naphthyl-(2)-oxy)-ethyl)-3-ethoxycarbonylamino-pyrazol-one-(5) in 200 ml of aqueous 2 N hydrochloric acid and the mixture was then boiled for 2 hours under reflux. After cooling, and neutralising with dilute sodium hydroxide solution, it was possible

| No. | Structural formula | Recrystallization from | Yield, % of theory | Melting point °C |
|---|---|---|---|---|
| 26 | 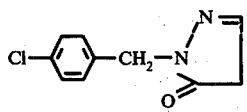 | Ethanol | 40 | 190 |

From: 3,4-di-chlorobenzylhydrazine + α-phenyl-β-amino-β-ethoxyacrylic acid ethyl ester

EXAMPLE 27

(1-(4-chloro-benzyl)-pyrazol-5-one)

9.8 g (0.1 mol) of propiolic acid ethyl ester and 15.6 g (0.1 mol) of p-chlorobenzylhydrazine in 100 ml of n-butanol were heated for 8 hours under reflux.

The solution was concentrated and the oily residue was triturated with a mixture of ethanol and ether to filter off a crystalline product. This was recrystallized from methanol.

Melting point 133°-135° C; yield 20.2 g (75% of theory).

What is claimed:

1. A compound of the formula

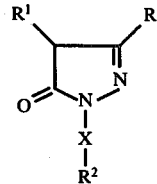

I or a pharmaceutically acceptable, nontoxic salt thereof, wherein

R is amino;

$R^1$ is monoaryl unsubstituted or substituted by lower alkoxy or aralkyl wherein the aryl moiety is a monoaryl moiety and the alkyl moiety is a lower alkyl moiety, said aralkyl being unsubstituted or substituted by lower alkoxy;

X is
 a. ethylene, ethylene wherein 1 hydrogen atom on one of the carbon atoms is substituted by alkyl of 1 to 4 carbon atoms or ethylene wherein 1 hydrogen atom on each of the two carbon atoms is substituted by alkyl of 1 to 4 carbon atoms;
 b. propenyl or propenyl wherein 1 hydrogen atom on one, two or three of the carbon atoms is substituted by alkyl of 1 to 4 carbon atoms; or
 c. methylene;

$R^2$ is aryl of 6 to 10 carbon atoms unsubstituted or substituted by:
 a. 1 or 2 of the same or different substituents selected from the group consisting of halogen, trifluoromethyl, alkyl of 1 to 8 carbon atoms, alkenyl of 2 to 8 carbon atoms and lower alkoxy;
 b. cycloalkyl of 5, 6 or 7 carbon atoms or cycloalkenyl of 5, 6 or 7 carbon atoms;
 c. nitro; or
 d. nitro and 1 or 2 of the same or different substituents selected from the group consisting of lower alkyl, lower alkenyl, lower alkoxy, halogen and trifluoromethyl.

2. A compound according to claim 1 wherein $R^1$ is phenyl unsubstituted or substituted by lower alkoxy or benzyl unsubstituted or substituted by lower alkoxy; and $R^2$ is aryl of 6 to 10 carbon atoms unsubstituted or substituted by:
 a. 1 or 2 of the same or different substituents selected from the group consisting of halogen, trifluoromethyl, alkyl of 1 to 4 carbon atoms, alkenyl of 2 to 4 carbon atoms and alkoxy of 1 to 4 carbon atoms;
 b. nitro; or
 c. nitro and 1 or 2 of the same or different substituents selected from the group consisting of alkyl of 1 to 4 carbon atoms, alkenyl of 2 to 4 carbon atoms, alkoxy of 2 to 4 carbon atoms, halogen and trifluoromethyl.

3. A compound according to claim 1 wherein $R^1$ is phenyl unsubstituted or substituted by alkoxy of 1 to 4 carbon atoms or benzyl unsubstituted or substituted by alkoxy of 1 to 4 carbon atoms;

X is
 a. ethylene, ethylene wherein 1 hydrogen atom on one of the carbon atoms is substituted by alkyl of 1 to 4 carbon atoms or ethylene wherein 1 hydrogen atom on each of the two carbon atoms is substituted by alkyl of 1 to 4 carbon atoms;
 b. propenyl or propenyl wherein 1 hydrogen atom on one or two of the carbon atoms is substituted by alkyl of 1 to 4 carbon atoms; or
 c. methylene; and $R^2$ is phenyl; naphthyl; or phenyl substituted by:
 a. 1 or 2 straight or branched-chain alkyl moieties of 1 to 8 carbon atoms, or alkenyl moieties of 2 to 8 carbon atoms;
 b. 1 or 2 alkoxy moieties of 1 to 6 carbon atoms;
 c. cycloalkyl of 5, 6 or 7 carbon atoms or cycloalkenyl of 5, 6 or 7 carbon atoms;
 d. 1 or 2 halogens;
 e. 1 or 2 trifluoromethyl moieties; or
 f. nitro.

4. A compound according to claim 1 wherein $R^1$ is phenyl, benzyl, or phenyl or benzyl substituted by alkoxy of 1 or 2 carbon atoms;

X is
 a. ethylene, ethylene wherein 1 hydrogen atom on one of the carbon atoms is substituted by alkyl of 1 to 4 carbon atoms or ethylene wherein 1 hydrogen atom on each of the two carbon atoms is substituted by alkyl of 1 to 4 carbon atoms;
 b. propenyl or propenyl wherein 1 hydrogen atom on one or two of the carbon atoms is substituted by alkyl of 1 to 4 carbon atoms; or
 c. methylene; and $R^2$ is phenyl; naphthyl; or phenyl substituted by:
 a. 1 or 2 straight or branched-chain alkyl moieties of 1 to 4 carbon atoms or alkenyl moieties of 2 to 4 carbon atoms;
 b. 1 or 2 alkoxy moieties of 1 to 4 carbon atoms;
 c. cycloalkyl of 5, 6 or 7 carbon atoms or cycloalkenyl of 5, 6 or 7 carbon atoms;
 d. 1 or 2 fluoro, chloro or bromo moieties;
 e. 1 or 2 trifluoromethyl moieties; or
 f. nitro.

5. A compound according to claim 1 wherein $R^1$ is phenyl or benzyl;

X is
 a. ethylene, ethylene wherein 1 hydrogen on one of the carbon atoms is substituted by alkyl of 1 to 4 carbon atoms or ethylene wherein 1 hydrogen atom on each of the two carbon atoms is substituted by alkyl of 1 to 4 carbon atoms;
 b. propenyl or propenyl wherein 1 hydrogen atom on 1 of the carbon atoms is substituted by alkyl of 1 to 4 carbon atoms; or
 c. methylene; and $R^2$ is phenyl; naphthyl; or phenyl substituted by:
 a. 1 or 2 members selected from the group consisting of straight or branched-chain alkyl and trifluoromethyl moieties of 1 to 4 carbon atoms;
 b. alkoxy of 1 to 4 carbon atoms;
 c. cycloalkyl of 5 or 6 carbon atoms;
 d. 1 or 2 fluoro, chloro, bromo or iodo moieties;
 e. chloro or bromo and alkyl of 1 or 2 carbon atoms or trifluoromethyl; or
 f. nitro.

6. A compound according to claim 1 wherein $R^1$ is phenyl or benzyl;

X is
 a. ethylene, ethylene wherein 1 hydrogen atom on one of the carbon atoms is substituted by alkyl of 1 or 2 carbons or ethylene wherein 1 hydrogen atom on each of the two carbon atoms is substituted by alkyl of 1 or 2 carbon atoms;
 b. propenyl or propenyl wherein 1 hydrogen atom on one of the carbon atoms is substituted by alkyl of 1 or 2 carbon atoms; or
 c. methylene; and $R^2$ is phenyl; naphthyl; or phenyl substituted by fluorine, chlorine, bromine, iodine, trifluoromethyl, nitro, alkyl of 1 to 4 carbon atoms, alkoxy of 1 to 4 carbon atoms, cyclohexyl, dichlorine, chlorine and methyl, chlorine and bromine, chlorine and fluorine, chlorine and trifluoromethyl, dibromine or methyl and trifluoromethyl.

7. A compound according to claim 6 wherein X is
   a. ethylene, ethylene wherein 1 hydrogen on one of the carbon atoms is substituted by methyl or ethyl or ethylene wherein 1 hydrogen atom on each of the two carbon atoms is substituted by methyl;
   b. propenyl or propenyl wherein 1 hydrogen on one of the carbon atoms is substituted by methyl; or
   c. methylene.

8. A compound according to claim 1 wherein
R¹ is phenyl;
X is
   a. ethylene;
   b. propenyl; or
   c. methylene;
R² is phenyl; naphthyl; or phenyl substituted by 1 or 2 chlorine, methyl, ethyl or trifluoromethyl moieties.

9. A compound according to claim 1 wherein
R¹ is phenyl;
X is
   a. ethylene;

R² is naphthyl, phenyl or phenyl substituted by chlorine, methyl, trifluoromethyl, dichlorine, dimethyl, methyl and ethyl or methyl and trifluoromethyl.

10. The compound according to claim 1 which is

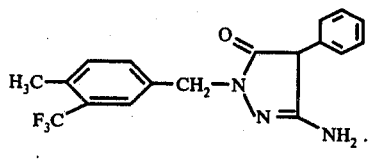

11. The compound according to claim 1 which is

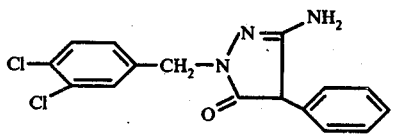

* * * * *